United States Patent [19]

Eisenstadt

[11] Patent Number: 4,983,754

[45] Date of Patent: Jan. 8, 1991

[54] METHOD FOR THE MANUFACTURE OF DIMETHYL, OCTYL - OR PENTYL - PARA-AMINOBENZOIC ACID

[75] Inventor: Amihai Eisenstadt, Ramat Hasharon, Israel

[73] Assignee: Bromine Compounds Ltd., Beer-Sheva, Israel

[21] Appl. No.: 280,134

[22] Filed: Dec. 5, 1988

[30] Foreign Application Priority Data

Dec. 7, 1987 [IL] Israel .................................. 84736

[51] Int. Cl.$^5$ ............................................ C07C 101/00
[52] U.S. Cl. ................................................ 560/19
[58] Field of Search ........................................ 560/19

[56] References Cited

U.S. PATENT DOCUMENTS

| | | | |
|---|---|---|---|
| 2,640,071 | 5/1953 | Leibu | 260/475 |
| 3,403,207 | 8/1968 | Kreps | 424/60 |
| 3,988,358 | 10/1976 | Heck | 560/19 |
| 4,654,436 | 3/1987 | Lane et al. | 560/80 |

OTHER PUBLICATIONS

"Activation of Reducing Agents, Sodium Hydride Containing Complex Reducing Agents...", J. J. Brunet, et al., *Journal of Organic Chemistry,* vol. 44, No. 13, 1979, p. 2199.

*Primary Examiner*—Bruce Gray
*Attorney, Agent, or Firm*—Morgan & Finnegan

[57] ABSTRACT

A method for the manufacture of dimethyl octyl (or pentyl) para-amino benzoic acid is described. The method consists in the carbonylation of para-bromo-dimethyl aniline, in the absence of any promoter, in a reaction system having a pH of above 8 in the presence of an alcohol selected from octanol, pentanol or isomers thereof using a palladium catalyst on an inert support. The reaction is carried out at a temperature in the range of 140° to 200° C. and a pressure of between 1 to 5 atmospheres. The product obtained is characterized by its high purity being substantially free of any impurities.

9 Claims, No Drawings

METHOD FOR THE MANUFACTURE OF DIMETHYL, OCTYL - OR PENTYL - PARA-AMINOBENZOIC ACID

The present invention relates to an improved method for the manufacture of reagents adapted for application as sun screening substances. More particularly the invention relates to an improved method for the manufacture of dimethyl-octyl (or pentyl) —p-aminobenzoic esters which are substantially pure.

BACKGROUND OF THE INVENTION

In U.S. Pat. No. 3,403,207 (S.I. Kreps et.al.) are disclosed sun screen compositions based on derivatives of para-aminobenzoic esters. The common preparation of these esters is carried out by esterification of the corresponding acid using the appropriate alcohol. The particular acid can be obtained by reductive methylation of p-nitrobenzoic acid in an ethanolic solution. Another process for directly obtaining the esters comprises the N-methylation of p-aminobenzoic acid using a system based on $Me_2SO_4$ - KOH (cf chemical Abstracts 77, 5110K).

An interesting process is described in J.Org.Chem. 44 (13), 2199, 1979, in which the carbonylation of p-Br-dimethylaniline is carried out with CO in the presence of a catalyst based on $NaH-RONaCo(OAc)_2$. The process has the disadvantage that products with very low carbonylation yields (35–40%) and high content of impurities are obtained.

In U.S. Pat. No. 2,640,071 a method is described for the preparation of carboxylic acid derivatives based on the carbonylation of aromatic halides. The reaction is catalyzed by compounds of metals from group VIII at temperatures in the range of 250 to 450° C. and carbon monoxide pressures in the range of 300 to 1000 atmospheres.

In a very recent U.S. Pat. No. 4,654,436, aromatic carboxylic acid esters are obtained by reacting an aromatic halide, such as benzene halide, naphthalene halide, with carbon monoxide in the presence of a palladium catalyst promoted with metal carbonyls, said metal being selected from group VIB. As mentioned in the specification, the most preferred reaction temperatures are in the range of between 100° to 125° C. From the Examples given, conversions in the range of 67% to 95% are claimed to be obtained, but no data are specified concerning the impurities present in the products. However, it is stipulated and exemplified in the specification, that in the absence of a promoter very poor conversions in the order of 16% to 20% are obtained.

It should be clearly understood that for human skin protection, the problem of impurities present in the reagents used therein is very critical.

It is an object of the present invention to provide a simple method for the manufacture of dimethyl-octyl (or pentyl) para- aminobenzoic ester. It is another object of the present invention to provide a simple method for the manufacture of the above compounds at very high conversions. It is yet another object of the present invention to provide a simple method for the manufacture of the above compounds in a substantially pure form.

BRIEF DESCRIPTION OF THE INVENTION

The invention relates to a method for the manufacture of dimethyl octyl (or pentyl) para-aminobenzoic esters which comprises the carbonylation of p-bromodimethylaniline in a reaction system having a pH of above 8 in the presence of an alcohol selected from octanol, pentanol and isomers thereof using a palladium catalyst. It was unexpectedly found that according to this method very high yields of above 80% and even above 90% are achieved. Moreover, the products obtained are very pure being substantially free of impurities as shown by gas chromatography analysis.

The catalytic reaction goes very smoothly without requiring any promoter, suggested in reactions using the palladium catalytic system.

It was found that a certain amount of carbonylation of the substrate occurred in the presence of the promoter, but before the start of the introduction the carbon monooxide into the heated mixture. Accordingly, a certain conversion of the bromosubstrate to the corresponding ester resulted from its stoichiometric reaction with the coordinated (CO) ligands of the promoter molecule, without any connection to the catalytic process. This of course is quite undesirable; Example 6 illustrates this point.

The alcohol used in the reaction has a two-fold purpose: first, use as reaction medium and second to participate in the formation of the corresponding ester.

The reaction conditions may be varied over a very broad range of temperatures and pressures. Of course lower temperatures will require a longer reaction time. Preferred temperatures will be in the range of between 140 to 200° C. and most preferred in the range of between 160 to 170° C. It was found that the preferred temperature is quite important concerning the high conversions and for reduction of the reaction time. This is illustrated in Example 5. Generally, the reaction will be complete after 2 to 12 hours depending on the temperature prevailing in the reactor. The pressure in the reaction system is quite uncritical and even atmospheric or slightly above, will be sufficient, the purpose being to assist the carbonylation by the carbon monoxide. Most preferred pressures will be in the range of 1 to 4 atmospheres. This is of great importance from a technological point of view since robust autoclaves are not required. This feature, is also contrary to known methods where pressures of about 10 to 1000 atmospheres, are stated as required during the carbonylation reaction.

The catalyst to be used is palladium metal on an inert support, most preferably carbon. The amount of palladium present is about 0.1% to 0.3% mole based on the p-bromodimethylaniline introduced in the reaction.

One of the requirements of the reaction is a basic medium with a pH above 8. This may be accomplished by adding a common alkaline substance such as sodium or potassium carbonate, calcium or magnesium oxide, calcium or magnesium carbonate or any mixture thereof. The alkaline reagent is preferably added in a solid state, the presence of an aqueous medium being most undesirable for the ester preparation The amount of alkali will depend on the reagent used, generally being in the range of between 1 to 1.6 mole to 1 mole of the p-bromo-dimethylaniline introduced in the reaction.

It was unexpectedly found that aromatic halides such as bromobenzene or dibromobenzene, mentioned in the prior art as starting reagents for this type of reaction, give lower conversion rates in a given reaction time compared with the p-bromodimethylaniline. Moreover, the product obtained will contain various impurities (such as aldehydes, coupling products etc.). This will be illustrated in the experimental section by Example 2 carried out under the conditions of the present invention except with replacement of the organic halide by the bromobenzene.

An important advantage of the method is the fact that the alcohol and the catalyst (palladium on carbon support) can be recycled. This clearly has a beneficial effect on the economy of the method. A detailed description of this embodiment is illustrated in Example 8.

The entire method is very simple and requires common equipment. The reagents: p-bromodimethylaniline, an alkaline compound (in a solid form), the palladium on an inert support and the alcohol are introduced into a reactor. The mixture is agitated and flushed with nitrogen gas followed by bubbling therein carbon monoxide, the reactor being maintained with stirring at a temperature range of between 130–180° C. At the end of the reaction, the reactor is cooled and vented and water is added separating out an organic layer. This layer is subsequently subjected to fractional distillation whereby the respective ester, of a very high purity is obtained.

The process may be carried out in the presence of inert solvents as media of reaction, although generally these are not necessary, since the alcohol employed in the reaction will also fulfill this function.

Summing up, the novel method according to the present invention provides improved rates of conversion and high purity of the products. Accordingly, the products obtained after distillation can be utilized directly for human skin protection such as sun-screen reagents, without requiring any additional purification step. While the invention will now be described in connection with certain preferred embodiments in the following Examples, it will be understood that it is not intended to limit the invention to these particular embodiments. On the contrary, it is intended to cover all alternatives, modifications and equivalents as may be included within the scope of the invention as defined by the appended Claims. Thus the following Examples which include preferred embodiments will serve to illustrate the practice of this invention, it being understood that the particulars described are by way of example and for purposes of illustrative discussion of preferred embodiments of the present invention only.

In the Examples the percentages given are by weight unless otherwise stated. Examples 2, 5 and 6 do not illustrate the invention and are presented only for comparison purpose. The gas chromatography analyses were carried out on a HP 5890 A instrument using a SE 30 capillary containing 100% dimethyl siloxane.

EXAMPLE 1

The reactor consisted of a 300 ml round-bottomed flask equipped with a condenser, thermometer, gas bubbler and a sampler device.

The following reagents were introduced into the reactor:
15 g of p-bromo-dimethylaniline (p-BrDMA).
6 g of sodium carbonate (solid form).
128 mg of palladium on carbon support (10%), and
160 ml of 2-ethyl-1-hexanol.

The mixture was flushed with nitrogen for about forty minutes then heated at 160° C. for about 5 hours while a stream of carbon monoxide was bubbled in, under continuous stirring. A sample taken out from the reactor indicated a conversion of 97% as shown by gas chromoatography. After the reactor was cooled and vented, about 100 ml of water were added and the whole mixture was filtered. The organic layer was separated and subjected to fractional distillation, whereby 16.6 g of dimethyloctyl-p-amino-benzoic ester were obtained with a purity of above 98.5%.

EXAMPLE 2

The experiment as in Example 1 was repeated using the same reactor, amounts and reaction conditions except that instead of p-bromo-dimethyl aniline, 15 g of p-bromobenzene were utilized. In this experiment, the conversion into the product was only 80% and the percentage of impurities was much higher than in Example 1.

EXAMPLE 3

The operation was carried out in the same equipment and according to the same method as Example 1.

A mixture of 6 g (0,03 M) p-bromo-N,N.-dimethylaniline, 2.4 g (0.023 M) sodium carbonate, 60 ml 2-ethyl-1-hexanol and 106.5 mg Pd/C (10%) was carbonylated under 1 Atm, pressure of carbon monoxide at 160–165 C. After four hours, the conversion into the product was 96%.

EXAMPLE 4

Example 1 was repeated except that the catalyst used consisted of 212 mg Pd/C (5%). Over 99% conversion of the p-bromo-dimethylaniline occurred after four hours and about 97% of the pure product was detected.

EXAMPLE 5

Example 2 was repeated except that the reaction mixture was heated to 125 C, instead of 160–170 C. About 54% product was detected after 5 hours reaction time.

EXAMPLE 6

The experiment as described in the U.S. Pat. No. 4,654,436 was performed in the equipment as in Example 1. 5.07 g p-BrDMA, 2.1 g $Na_2CO_3$, 0.193 g Pd/C (4.5%) and 0.193g $Mo(CO)_6$ were introduced into a 100cc glass reactor with 50 ml 2-ethyl-1-hexanol and the mixture was heated to 125° C. under a $N_2$ atmosphere for 30 min. At this stage, a conversion of about 16% ester was detected although CO had not yet been introduced. A sample was taken out and found to contain other by-products together with the desired ester.

A stream of carbon monoxide was introduced into the reaction mixture and further heated at 125° C. for 3 hours. The total yield of ester formed in the reaction was 73.7%.

EXAMPLE 7

The experiment as in Example 6 was repeated, using the same amounts of reagents but without the promoter, the reaction being carried out at 165° C.

The conversion to the ester formed after about 3 hours was 95%.

EXAMPLE 8

(Multicycled-alkoxycarbonylation of p-BrDMA).

Four batches of the ester were prepared recycling the Pd/C and the alcohol each time.

The following components were used in each cycle of the alkoxycarbonylation: 40.5 g p-BrDMA (0.203 M), 16.5 g $Na_2CO_3$ (0.157 M), 400 ml (428 g) 2-ethyl-1-hexanol (recovered from a previous cycle), and 102 mg fresh Pd/C, (in addition to the 1.043 g 4.5% Pd/C used in the first cycle). A stream of carbon monoxide (20 ml/min) was applied during the reaction at 169–173° C., with mechanical stirring.

The Pd/C from the previous cycle was washed with water and acetone then dried and used on a fresh batch of p-Br-dimethyl-aniline along with 20% fresh Pd/C. The 2-ethyl-1-hexanol was distilled from the reaction mixture and reused for the next batch. A further portion of 10% Pd/c was added before the end of the first three runs to finish off the starting material. It was found that each run took 12–14 hours, where the last 3–4 hours were required for only 5–8% unreacted starting material. The total amount of Pd metal used throughout the 4-cycle process corresponds to a substrate/Pd molar ratio of 1298.

Distillation of the 4-cycle batch of the ester gave an overall yield of 71.45% with a purity of above 99.5%. Quantitative analysis of the oily crude residue prior to the distillation revealed an optimal yield (86.5%) of the desired product.

The total Pd/C waste filtered from the 4-cycle process was washed with ethyl acetate and distilled water and dried in a vacuum oven, then analysed for Pd metal; 63.7% of the Pd used for the four carbonylation cycles were found.

I claim:

1. A method for the manufacture of an ester selected from the group consisting of dimethyl octyl-p-aminobenzoic acid and dimethyl pentyl p-aminobenzoic acid which comprises the carbonylation of p-bromodimethyl aniline in the absence of any promoter in a reaction system having a pH of above 8 in the presence of an alcohol selected from octanol, pentanol or isomers thereof, using a palladium catalyst on an inert support.

2. A method according to claim 1, wherein said inert support is carbon.

3. A method according to claim 1, carried out at a temperature in the range of 140 to 200° C.

4. A method according to claim 1, carried out at a pressure in the range of 1 to 5 atmospheres.

5. A method according to claim 1, carried out at a temperature in the range of 160° to 170° C.

6. A method according to claim 1, wherein the pH of above 8 is obtained by the incorporation of an alkaline substance.

7. A method according to claim 6, wherein the alkaline substance is selected from the group consisting of potassium carbonate, sodium carbonate, calcium oxide, magnesium oxide, magnesium carbonate, calcium carbonate and mixtures thereof.

8. A method according to claim 6, wherein the amount of alkaline substance is in the range of between 1 to 1.6 moles to 1 mole of para-bromodimethyl-aniline.

9. A method according to claim 1, wherein the alcohol and palladium catalyst are recycled.

* * * * *